(12) United States Patent
Junghans

(10) Patent No.: US 7,662,990 B2
(45) Date of Patent: Feb. 16, 2010

(54) PROCESS FOR PREPARING IBANDRONATE

(75) Inventor: Bernd Junghans, Edingen-Neckarhausen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/060,314

(22) Filed: Apr. 1, 2008

(65) Prior Publication Data

US 2008/0255386 A1     Oct. 16, 2008

(30) Foreign Application Priority Data

Apr. 11, 2007   (EP) .................................. 07105915

(51) Int. Cl.
*C07F 9/38* (2006.01)
(52) U.S. Cl. ....................................................... 562/13
(58) Field of Classification Search ........................ None
See application file for complete search history.

(56) References Cited

U.S. PATENT DOCUMENTS

| | | |
|---|---|---|
| 3,919,321 A | 11/1975 | Kyburz et al. |
| 4,054,598 A | 10/1977 | Blum et al. |
| 4,220,611 A | 9/1980 | Wolf |
| 4,876,339 A | 10/1989 | Blum et al. |
| 4,927,814 A | 5/1990 | Gall et al. |
| 4,942,157 A | 7/1990 | Gall et al. |
| 5,002,937 A | 3/1991 | Bosies et al. |
| 7,214,818 B2 | 5/2007 | Baetz et al. |
| 2006/0172975 A1 | 8/2006 | Eiermann et al. |
| 2006/0172976 A1 | 8/2006 | Eiermann et al. |

FOREIGN PATENT DOCUMENTS

| | | |
|---|---|---|
| EP | 252 504 | 1/1988 |
| EP | 332 068 | 9/1989 |
| EP | 350 002 | 1/1990 |
| EP | 402 152 | 12/1995 |
| GB | 1540238 | 2/1979 |
| WO | WO 01/57052 | 8/2001 |
| WO | WO 03/097655 | 11/2003 |
| WO | WO 2005/063779 | 7/2005 |
| WO | WO 2006/002348 | 1/2006 |
| WO | WO 2006/024024 | 3/2006 |
| WO | WO 2006/045578 | 5/2006 |
| WO | WO 2007/013097 | 2/2007 |

OTHER PUBLICATIONS

Widler, L., et al., Journal of Medicinal Chemistry, vol. 45, No. 17, pp. 3721-3738 (2002).
Hale, W. J., et al., Journal of the American Chemical Society, vol. 42, No. 1, pp. 107-116 (1920).
Galin, F.Z., et al., Bulletin of the Academy of Sciences of the USSR, Division of Chemical Science, vol. 37, No. 4, pp. 708-712 (1988).
Freifelder, M., et al., Journal of the American Chemical Society, vol. 80, No. 16, pp. 4320-4323 (1958).
Kieczykowski G R et al, *Jour. of Organic Chem*, 60:25 (1995) 8310-8312.

*Primary Examiner*—Daniel M Sullivan
*Assistant Examiner*—Yevegeny Valenrod
(74) *Attorney, Agent, or Firm*—George W. Johnston; Patricia S. Rocha-Tramaloni; David E. Wildman

(57) ABSTRACT

The invention relates to a novel multi step synthesis of 3-(N-methyl-N-pentyl)amino-1-hydroxypropane-1,1-diphosphonic acid, monosodium salt, monohydrate, of the formula

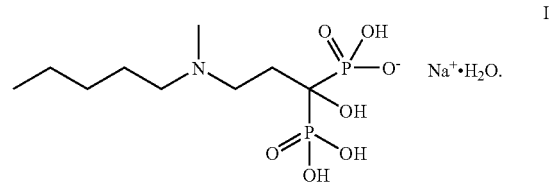

I

11 Claims, No Drawings

PROCESS FOR PREPARING IBANDRONATE

PRIORITY TO RELATED APPLICATION(S)

This application claims the benefit of European Patent Application No. 01705915.8, filed Apr. 11, 2007 which is hereby incorporated by reference in its entirety.

The present invention relates to a process for the preparation of 3-(N-methyl-N-pentyl)amino-1-hydroxypropane-1,1-diphosphonic acid, monosodium salt, monohydrate (Ibandronate) with the formula I:

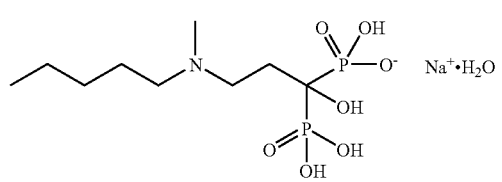

Ibandronate is one of the most potent antiresorptive drugs that directly inhibit osteoclast activity and present an effective pharmacologic alternative for controlling hypercalcemia. Ibandronate binds to hydroxyapatite in calcified bone, rendering it resistant to hydrolytic dissolution by phosphatases, thereby inhibiting both normal and abnormal bone resorption. This drug increases bone mass and decreases the risk of fractures and is therefore particularly well adapted to bone and calcium metabolic diseases such as for instance osteoporosis or Paget's disease (see, e.g., U.S. Pat. No. 4,927,814)

A number of processes for the preparation of Ibandronate are known in the art.

U.S. Pat. No. 7,214,818 discloses a multistep process for the preparation of Ibandronate which requires the formation of the hydrohalogenide after the hydrolysis of the N-methyl-N-pentyl-β-alanine methyl ester before the bisphosphorylation can be effected. It was found that the hydrohalogenide formation lowers the overall effectiveness and the yield of the process.

The present invention, inter alia, improves upon the yield of the process set forth in U.S. Pat. No. 7,214,818, as outlined below.

In one embodiment the process of the present invention comprises hydrolyzing N-methyl-N-pentyl-β-alanine methyl ester to produce N-methyl-N-pentyl-β-alanine of formula IV

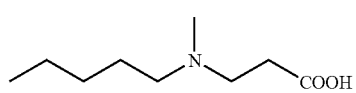

and subsequently bisphosphorylating the compound of formula IV by contacting the compound of formula IV with phosphoryl chloride and phosphorous to yield 3-(N-methyl-N-pentyl)amino-1-hydroxypropane-1,1-diphosphonic acid and forming the monosodium salt, monohydrate of 3-(N-methyl-N-pentyl)amino-1-hydroxypropane-1,1-diphosphonic acid In a further embodiment the process of the present invention comprises:

(a) condensing N-pentylamine with benzaldehyde to produce the N-benzylidene-N-pentylamine of formula II

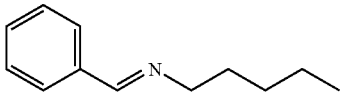

(b) transforming the N-benzylidene-N-pentylamine into N-methyl-N-pentylamine by contacting N-benzylidene-N-pentylamine with a methylating agent (c) contacting N-methyl-N-pentylamine with methyl acrylate to yield N-methyl-N-pentyl-β-alanine methylester of formula III

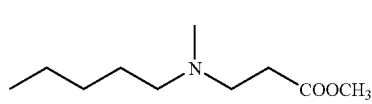

(d) hydrolyzing N-methyl-N-pentyl-β-alanine methyl ester to produce the N-methyl-N-pentyl-β-alanine of formula IV

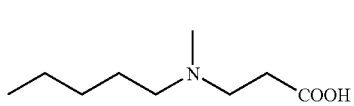

(e) bisphosphorylating the compound of formula IV by contacting the compound of formula IV with phosphoryl chloride and phosphorous acid to yield 3-(N-methyl-N-pentyl)amino-1-hydroxypropane-1,1-diphosphonic acid; and (f) forming the monosodium salt, monohydrate of 3-(N-methyl-N-pentyl)amino-1-hydroxypropane-1,1-diphosphonic acid.

The first step a) of the process of the present invention comprises the condensation of N-pentylamine with benzaldehyde to produce the N-benzylidene-N-pentylamine of formula II.

This condensation can be carried out in a suitable solvent such as aliphatic alcohols, at a reaction temperature of 40° C. to 90° C., preferably in methanol at 70° C. to 75° C.

The second step b) of the process of the present invention comprises transformation of the N-benzylidene-N-pentylamine into the N-methyl-N-pentylamine with a methylating agent.

Methylating agents such as methyl halogenides or dimethyl sulfate, but preferably dimethyl sulfate is used. The reaction as a rule takes place at a temperature of 80° C. to 110° C., preferably at 90° C. to 100° C. The generated benzaldehyde can optionally be removed by steam distillation and the resulting N-methyl-N-pentylamine can be isolated from the aqueous phase by any means known to the skilled in the art such as by addition of a base and extraction of the basic solution with a suitable organic solvent such as aliphatic ethers, but preferably with diisopropylether. The product can be further purified for instance by distillation.

In the third step (c) of the process of the present invention the N-methyl-N-pentylamine is contacted with methyl acrylate to yield N-methyl-N-pentyl-β-alanine methylester of formula III.

This reaction can be carried out in a suitable solvent such as aliphatic alcohols, aliphatic ethers or ether/alcohol mixtures, but preferably in methanol at a reaction temperature of 10° C.

to 65° C., preferably at 15° C. to 25° C. Isolation of the N-methyl-N-pentyl-β-alanine methyl ester can be performed by techniques known to the skilled in the art such as distillation.

Step (d) of the process of the present invention requires the hydrolysis of N-methyl-N-pentyl-β-alanine methyl ester to produce the N-methyl-N-pentyl-β-alanine of formula IV.

The hydrolysis is performed in water at temperatures from 90° C. to 100° C. at least until no educt ester can be detected. The free base can be isolated either by removing water by distillation, addition of a suitable solvent, preferably diethylcarbonate, and azeotropic distillation to remove residual water or by way of extracting the reaction mixture with a suitable solvent such as with diethylcarbonate and subsequent azeotropic distillation to remove residual water.

The solution of N-methyl-N-pentyl-β-alanine so obtained can directly be used for the subsequent bisphosphorylation step.

Step (e) of the present invention comprises the bisphosphorylation of the compound of formula IV by means of phosphoryl chloride and phosphorous acid and the formation of the monosodium salt, monohydrate.

The bisphosphorylation of the N-methyl-N-pentyl-β-alanine may take place either without the presence of a non aromatic solvent or in the presence of a suitable solvent. It is preferred to use a solvent.

Suitable non aromatic solvents are phosphoric acid esters, phosphonic acid esters or carbonic acid esters, preferred solvent is diethylcarbonate.

As phosphorylating agent a mixture of phosphoryl chloride and phosphorous acid is used. The molar ratio N-methyl-N-pentyl-β-alanine:phosphoryl chloride:phosphorous acid is a rule selected from 1.0:3.0:3.0 to 1.0:1.4:2.4, preferably 1.0: 1.6:2.4 to 1:1.4:2.4

During the bisphosphorylation the reaction temperature is expediently maintained in a range of from 60° C. to 100° C., preferably 80° C. to 90° C.

After hydrolysis of the reaction mixture in case a non aromatic solvent is used it is ideally removed by separation from the aqueous phase.

In order to isolate the monosodium salt, monohydrate of the 3-(N-methyl-N-pentyl)amino-1-hydroxypropane-1,1-diphosphonic acid the pH of the remaining aqueous reaction mixture is adjusted to a pH from 3.5 to 6.0, preferably from 4.4 to 4.5 with an aqueous solution of sodium hydroxide at a temperature in range of 20° C. to 25° C.

The Ibandronate so obtained can be crystallized in suitable solvents such as aliphatic alcohols/water or aliphatic ketones/water, preferably in ethanol/water and acetone/water.

EXAMPLES a) Preparation of N-benzylidene-N-pentylamine 100 g (1.15 mol) N-pentylamine was added to 200 ml methanol at a temperature of 22° C. 121.8 g (1.15 mol) benzaldehyde was added. The mixture was refluxed and subsequently, methanol was distilled off. The residual N-benzylidene-N-pentylamine 199.8 g (99.4%) was used in the next step.

b) Preparation of N-methyl-N-pentylamine 60 g (475.7 mmol) dimethyl sulfate and 67 g (382.2 mmol) N-benzylidene-N-pentylamine were stirred at a temperature of 90-100° C. and 117 ml purified water was added to the mixture. The generated benzaldehyde was removed by steam distillation. 133 ml diisopropyl ether and 54 ml sodium hydroxide solution (50%) were added. The aqueous layer was separated. Diisopropyl ether was distilled off. 3.3 g sodium hydroxide flakes are added to the residue to bind residual water. The residue, crude N-methyl-N-pentylamine was purified by distillation (29.4 g; 76%).

c) Preparation of N-methyl-N-pentyl-β-alanine methyl ester 106 g (1.05 mol) N-methyl-N-pentylamine was added to cooled methanol of a temperature of 0-5° C. 108 g (1.25 mol) methyl acrylate was added to the solution and the mixture was stirred at room temperature for 8 hours. Then methanol was distilled off in vacuo and the residue was purified by distillation to obtain 188.6 g N-methyl-N-pentyl-β-alanine methyl ester (96.1%)

d1) Preparation of N-methyl-N-pentyl-β-alanine (Distillation Method)

68.8 g (367.4 mmol) N-methyl-N-pentyl-β-alanine methyl ester was hydrolyzed by refluxing with 138 ml water. Water was distilled off and 300 ml diethyl carbonate were added, followed by azeotropic distillation of diethyl carbonate/water (30 ml) to remove residual water. About 290 ml of a diethyl carbonate solution containing 63 g N-methyl-N-pentyl-β-alanine was obtained which could directly be used for the subsequent bisphosphorylation step.

d2) Preparation of N-methyl-N-pentyl-β-alanine (Extraction Method)

68.8 g (367.4 mmol) N-methyl-N-pentyl-β-alanine methyl ester was hydrolyzed by refluxing with 138 ml water. The aqueous reaction mixture was extracted with 3×100 ml diethyl carbonate, followed by azeotropic distillation of diethyl carbonate/water (30 ml) to remove residual water. About 290 ml of a diethyl carbonate solution containing 60 g N-methyl-N-pentyl-β-alanine was obtained which could directly be used for the subsequent bisphosphorylation step.

e) Preparation of 3-(N-methyl-N-pentyl)amino-1-hydroxypropane-1,1-diphosphonic acid, monosodium salt, monohydrate 60 g N-methyl-N-pentyl-β-alanine, dissolved in 290 ml diethylcarbonate, 68 g phosphorous acid and 45.6 ml phosphorus oxychloride were heated stepwise to 80° C. After 2 hours reaction time under continued heating the mixture was cooled to 60° C. and 600 ml purified water were added, followed by separation of the aqueous phase. 20 ml of water/residual diethylcarbonate were distilled off from the aqueous phase. The solution was cooled to 24° C. The pH was adjusted with sodium hydroxide solution (50%) to 4.4 at 23° C. Thereafter, 320 ml ethanol were added to start crystallization. The suspension was stirred for 8 hours at 21-22° C. Then crude 3-(N-methyl-N-pentyl)amino-1-hydroxypropane-1,1-diphosphonic acid, monosodium salt monohydrate was separated, washed with 100 ml cold ethanol/purified water (7/5), subsequently with 100 ml acetone/purified water (5/2) and dried at 60° C.

Yield: 97 g 3-(N-methyl-N-pentyl)amino-1-hydroxypropane-1,1-diphosphonic acid, monosodium salt crude (78%)

Purification 97 g 3-(N-methyl-N-pentyl)amino-1-hydroxypropane-1,1-diphosphonic acid, monosodium salt monohydrate crude were dissolved in 425 ml purified water. 130 ml water were distilled off. The solution was cooled to 49° C. and filtered. 340 ml acetone were added to the filtrate, followed by cooling to 20° C. and stirring for 8 hours. The crystallized 3-(N-methyl-N-pentyl)amino-1-hydroxypropane-1,1-diphosphonic acid, monosodium salt monohydrate pure was separated and washed with 120 ml acetone/purified water (1/1). Subsequently, it was dried in vacuo first 12 hours at 40° C., then 46 hours at 60° C., sieved and blended.

Yield: 77.6 g 3-(N-methyl-N-pentyl)amino-1-hydroxypropane-1,1-diphosphonic acid, monosodium salt monohydrate (80%)

Assay (complexometric titration): 100.7%

The invention claimed is:

1. A process for the preparation of 3-(N-methyl-N-pentyl)amino-1-hydroxypropane-1,1-diphosphonic acid, monosodium salt, monohydrate of the formula I

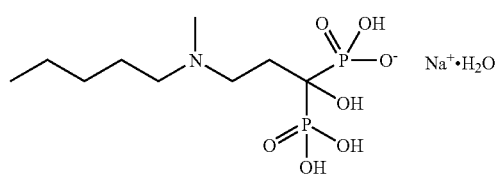

comprising:

hydrolyzing N-methyl-N-pentyl-β-alanine methyl ester in water to produce an aqueous solution of N-methyl-N-pentyl-β-alanine of formula IV

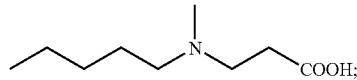

adding diethylcarbonate to the aqueous solution of the compound of formula IV;

azeotropically removing the water to yield a diethylcarbonate solution of the compound of formula IV;

bisphosphorylating the compound of formula IV by adding phosphoryl chloride and phosphorous acid to the diethylcarbonate solution of the compound of formula IV to yield 3-(N-methyl-N-pentyl) amino-1-hydroxypropane-1,1-diphosphonic acid; and forming the monosodium salt, monohydrate of 3-(N-methyl-N-pentyl) amino-1-hydroxypropane-1,1-diphosphonic acid.

2. A process for the preparation of 3-(N-methyl-N-pentyl)amino-1-hydroxypropane-1,1-diphosphonic acid, monosodium salt, monohydrate of formula I

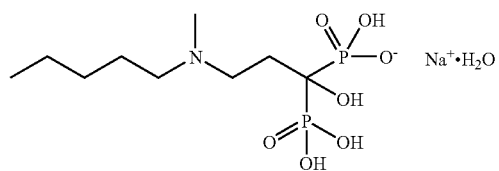

comprising:

(a) condensing N-pentylamine with benzaldehyde to produce N-benzylidene-N-pentylamine of formula II

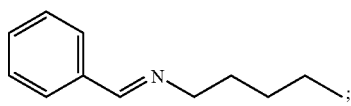

(b) transforming N-benzylidene-N-pentylamine into N-methyl-N-pentylamine by contacting N-benzylidine-N-pentylamine with a methylating agent;

(c) contacting N-methyl-N-pentylamine with methyl acrylate to yield the N-methyl-N-pentyl-β-alanine methyl ester of formula III;

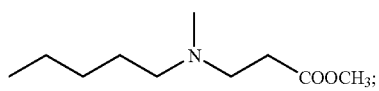

(d) hydrolyzing N-methyl-N-pentyl-β-alanine methyl ester in water to produce N-methyl-N-pentyl-β-alanine of formula IV

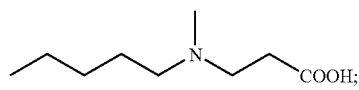

(e) adding diethylcarbonate to the solution of the compound of formula IV;

(f) azeotropically removing the water to yield a diethylcarbonate solution of the compound of formula IV;

(g) bisphosphorylating the compound of formula IV by adding phosphoryl chloride and phosphorous acid to the diethylcarbonate solution of the compound of formula IV to yield 3-(N-methyl-N-pentyl) amino-1-hydroxypropane-1,1-diphosphonic acid; and (h) forming the monosodium salt, monohydrate of 3-(N-methyl-N-pentyl) amino-1-hydroxypropane-1,1-diphosphonic acid.

3. The process according to claim 2, wherein the condensing in step (a) is performed in a suitable solvent at a temperature of 40° C. to 90° C.

4. The process according to claim 2 wherein the transforming in step (b) is performed at a temperature of 80° C. to 110° C.

5. The process according to claim 2 wherein the transforming in step (b) is performed with dimethyl sulfate as the methylating agent.

6. The process according to claim 2 wherein the contacting in step (c) is performed in a suitable solvent at a reaction temperature of between about 10° C. and about 65° C.

7. The process according to claim 2 wherein the hydrolyzing in step (d) is performed at a temperature of 90° C. to 100° C.

8. The process according to claim 2 wherein during the bisphosphorylating in step (g) the molar ratio N-methyl-N-pentyl-β-alanine phosphoryl chloride:phosphorous acid is selected from 1.0:3.0:3.0 to 1.0:1.4:2.4.

9. The process according to claim 2 wherein during the bisphosphorylating in step (g) the reaction temperature is between about 60° C. and about 100° C.

10. The process according to claim 1, wherein the monosodium salt, monohydrate of 3-(N-methyl-N-pentyl) amino-1-hydroxypropane-1,1-diphosphonic acid is formed in an aqueous reaction mixture by adjusting the pH of the aqueous reaction mixture to between about 3.5 and about 6.0 with an aqueous solution of sodium hydroxide.

11. The process according to claim 2, wherein the monosodium salt, monohydrate of 3-(N-methyl-N-pentyl) amino-1-hydroxypropane-1,1-diphosphonic acid is formed in an aqueous reaction mixture by adjusting the pH of the aqueous reaction mixture to between about 3.5 and about 6.0 with an aqueous solution of sodium hydroxide.

\* \* \* \* \*

UNITED STATES PATENT AND TRADEMARK OFFICE
CERTIFICATE OF CORRECTION

PATENT NO. : 7,662,990 B2
APPLICATION NO. : 12/060314
DATED : February 16, 2010
INVENTOR(S) : Bernd Junghans It is certified that error appears in the above-identified patent and that said Letters Patent is hereby corrected as shown below:

Claim 8, column 6, line 66, delete "pentyl-β-alanine phosphoryl chloride:phosphorous acid is"

and insert -- pentyl-β-alanine : phosphoryl chloride : phosphorous acid is --

Signed and Sealed this

Thirteenth Day of April, 2010

David J. Kappos
*Director of the United States Patent and Trademark Office*